US012570931B2

(12) United States Patent
Weber et al.

(10) Patent No.: US 12,570,931 B2
(45) Date of Patent: *Mar. 10, 2026

(54) **DISHWASHING AGENT WITH BLEACHING CATALYST AND *BACILLUS GIBSONII* PROTEASE**

(71) Applicant: Henkel AG & Co. KGaA, Duesseldorf (DE)

(72) Inventors: Thomas Weber, Weimar (DE);
Thorsten Bastigkeit, Wuppertal (DE);
Susanne Wieland, Zons/Dormagen
(DE); Christian Degering, Erkrath
(DE); Nina Mussmann, Willich (DE);
Thomas Doering, Dormagen (DE);
Melanie Mueller, Monheim (DE);
Silke Menke, Haan (DE); **Melanie
Szemait, Duisburg (DE); Claudia
Ottow**, Ratingen (DE)

(73) Assignee: Henkel AG & Co. KGaA, Düsseldorf
(DE)

( * ) Notice: Subject to any disclaimer, the term of this
patent is extended or adjusted under 35
U.S.C. 154(b) by 866 days.

This patent is subject to a terminal dis-
claimer.

(21) Appl. No.: 17/628,581

(22) PCT Filed: Jul. 16, 2020

(86) PCT No.: PCT/EP2020/070120
§ 371 (c)(1),
(2) Date: Jan. 20, 2022

(87) PCT Pub. No.: WO2021/013685
PCT Pub. Date: Jan. 28, 2021

(65) Prior Publication Data
US 2022/0251475 A1 Aug. 11, 2022

(30) Foreign Application Priority Data
Jul. 22, 2019 (EP) .................................... 19187517

(51) Int. Cl.
*C11D 3/386* (2006.01)
*C11D 3/39* (2006.01)
*C12N 9/52* (2006.01)

(52) U.S. Cl.
CPC ............ *C11D 3/386* (2013.01); *C11D 3/3905*
(2013.01); *C11D 3/3932* (2013.01); *C12N 9/52*
(2013.01)

(58) Field of Classification Search
None
See application file for complete search history.

(56) References Cited

U.S. PATENT DOCUMENTS

2004/0259222 A1    12/2004    Breves et al.
2005/0003419 A1     1/2005    Breves et al.

2009/0170745 A1     7/2009    Merkel et al.
2009/0275493 A1    11/2009    Siegert et al.
2014/0017763 A1     1/2014    Wieland et al.
2014/0106439 A1     4/2014    Mussmann et al.
2017/0247643 A1     8/2017    Eiting et al.
2019/0144792 A1     5/2019    Herbst et al.

FOREIGN PATENT DOCUMENTS

| | | | |
|---|---|---|---|
| CA | 2882331 A1 | 2/2014 | |
| CN | 104736703 A | 6/2015 | |
| DE | 102011005354 A1 | 9/2012 | |
| DE | 102011118037 A1 | 12/2012 | |
| EP | 0476257 A1 | 3/1992 | |
| EP | 0846155 A | 3/1997 | |
| GB | 1243784 A | 8/1971 | |
| WO | 9102792 A1 | 3/1991 | |
| WO | 9318140 A1 | 9/1993 | |
| WO | 9634946 A1 | 11/1996 | |
| WO | 0144452 A1 | 6/2001 | |
| WO | 0229024 A1 | 4/2002 | |
| WO | 03002711 A2 | 1/2003 | |
| WO | 03054177 A2 | 7/2003 | |
| WO | 03057246 A1 | 7/2003 | |
| WO | 03099985 A2 | 12/2003 | |
| WO | 2004031338 A1 | 4/2004 | |
| WO | 2007079938 A2 | 7/2007 | |
| WO | 2007131656 A1 | 11/2007 | |
| WO | 2008007319 A2 | 1/2008 | |
| WO | 2008086916 A1 | 7/2008 | |
| WO | WO-2012171980 A1 * | 12/2012 | ......... C11D 11/0023 |
| WO | 2016000973 A1 | 1/2016 | |

(Continued)

OTHER PUBLICATIONS

Ngo et al. in The Protein Folding Problem and Tertiary Structure
Prediction, 1994, Merz et al. (ed.), Birkhauser, Boston, MA, pp. 433
and 492-495.*
Franceus et al., J. Ind. Microbiol. Biotechnol. Vol 44, pp. 687-695,
2017.*
Search report from parallel European patent application No. 19 187
517.8 dated Nov. 13, 2019, 7 pages, for Information purpose only.
Search report from parallel PCT-application No. PCT/EP2020/
070120 dated Sep. 22, 2020, 7 pages, for Information purpose only.
Alan Tomlinson et al., "A Review of Key Ingredients Used in Past
and Present Auto-Dishwashing Formulations and the Physico-
Chemical Processes They Facilitate", Handbook for Cleaning/
Decontamination of Surfaces, 2007, bages 197-256, Elsevier B.V.
Siezen, Roland J., Subtilisin Enzymes, Subtilases: Subtilisin-Like
Serine Proteases, 1996, pp. 74-93, Plenum Press, New York.

(Continued)

*Primary Examiner* — Richard G Hutson
(74) *Attorney, Agent, or Firm* — Blank Rome LLP

(57) ABSTRACT

A dishwashing detergent may include a hydrogen peroxide
source, a bleach catalyst, and a protease. The protease may
include an amino acid sequence having at least 70%
sequence identity to the amino acid sequence given in SEQ
ID NO: 1 over its entire length and at least one amino acid
substitution at at least one of the positions corresponding to
positions 12, 43, 122, 127, 154, 156, 160, 211, 212, and 222,
relating in each case to the numbering according to SEQ ID
NO: 1.

15 Claims, No Drawings
Specification includes a Sequence Listing.

(56) References Cited

FOREIGN PATENT DOCUMENTS

WO          2017215925 A1    12/2017

OTHER PUBLICATIONS

Gornall et al., "Determination of Serum Proteins By Means of the Biuret Reaction", 1948, pp. 751-766, J. Biol. Chem.

Bender et al., "The Determination of the Concentration of Hydrolytic Enzyme Solutions: a-Chymotrypsin, Trypsin, Papain, Elastase, Subtilisin, and Acetylcholinesterase", 1966, pp. 5890-5913, Journal of the American Chemical Society, 88:24.

Altschul et al., "Basic Local Alignment Seach Tool", 1990, pp. 403-410, 215, J. Mol. Biol., Academic Press Limited.

Altschul et al., "Gapped BLAST and PSI-BLAST: a new generation of protein database search programs", 1997, pp. 3389-3402, vol. 25, No. 17, Nucleic Acids Research.

Chenna et al., "Multiple sequence alignment with the Clustal series of programs", 2003, pp. 3497-3500, vol. 31, No. 13, Nucleic Acids Research, Oxford University Press.

Notredame et al., "T-Coffee: A Novel Method for Fast and Accurate Multiple Sequence Alignment", 2000, pp. 205-217, J. Mol. Biol., Academic Press.

* cited by examiner

SEQUENCE LISTING

<160> NUMBER OF SEQ ID NOS: 1

<210> SEQ ID NO 1
<211> LENGTH: 269

-continued

```
<212> TYPE: PRT
<213> ORGANISM: Bacillus gibsonii

<400> SEQUENCE: 1

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
                20                  25                  30

Thr Gly Ile Ala Gln His Ser Asp Leu Thr Ile Arg Gly Gly Ala Ser
            35                  40                  45

Phe Val Pro Gly Glu Ser Thr Thr Ala Asp Leu Asn Gly His Gly Thr
        50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
            115                 120                 125

Pro Ser Thr Thr Leu Glu Arg Ala Val Asn Tyr Ala Thr Ser Arg Gly
        130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
            245                 250                 255

Phe Gly Ser Gly Leu Val Asn Ala Asp Ala Ala Thr Arg
            260                 265
```

DISHWASHING AGENT WITH BLEACHING CATALYST AND *BACILLUS GIBSONII* PROTEASE

REFERENCE TO A SEQUENCE LISTING SUBMITTED VIA EFS-WEB

The content of the ASCII text file of the sequence listing named "P82769US_SEQLTXT.txt", which is 3 kb in size was created on Jul. 22, 2019 and electronically submitted via EFS-Web herewith; the sequence listing is incorporated by reference in its entirety.

CROSS-REFERENCE TO RELATED APPLICATIONS

The present application is a national stage entry according to 35 U.S.C. § 371 of PCT Application No. PCT/EP2020/070120 filed on Jul. 16, 2020; which claims priority to European Patent Application Serial No. 19 187 517.8 filed on Jul. 22, 2019; all of which are incorporated herein by reference in their entirety and for all purposes.

TECHNICAL FIELD

The disclosure relates to dishwashing agent containing bleach, comprising at least one *Bacillus gibsonii* protease. The corresponding cleaning methods and the use of the agents described herein are also part of the disclosure.

BACKGROUND

The use of enzymes in detergents and cleaning agents has been established in the prior art for decades. They serve to expand the performance range of the agents in question according to their special activities. These include in particular hydrolytic enzymes such as proteases, amylases, lipases and cellulases. The first three mentioned hydrolyze proteins, starch and fats and thus contribute directly to the removal of dirt. Cellulases are used in particular because of their tissue effect. Proteases are the longest-established enzymes for practically all modern effective detergents and cleaning agents. This makes them one of the technically most important enzymes of all. Of these, in turn, proteases of the subtilisin type (subtilases, subtilopeptidases, EC 3.4.21.62) are particularly important and are serine proteases due to the catalytically active amino acids. They act as non-specific endopeptidases and hydrolyze any acid amide bonds that are inside peptides or proteins. Their optimum pH is usually in the distinctly alkaline range. An overview of this family is given, e.g., in the article "Subtilases: Subtilisin-like Proteases" by R. Siezen, pages 75-95 in "Subtilisin enzymes," published by R. Bott and C. Betzel, New York, 1996. Subtilases are, naturally, formed from microorganisms. In particular, the subtilisins formed and secreted by *Bacillus* species are the most significant group of subtilases. In detergents and cleaning agents, proteases are used to break down protein-containing stains on the items to be cleaned.

Dishwashing agents are available to the consumer in a plurality of product formats. In addition to the traditional liquid hand dishwashing detergents, with the spread of household dishwashers, automatic dishwashing detergents in particular have gained great importance. These automatic dishwashing agents are typically offered to the consumer in solid form, for example as a powder or as tablets.

One of the main goals of the manufacturers of automatic cleaning agents is to improve the cleaning performance of these agents, with more recent attention being paid to cleaning performance in low-temperature cleaning processes or in cleaning processes with reduced water consumption.

Protein-containing stains, in particular egg stains, and bleachable soiling, especially tea stains, however, represent stubborn stains that are often not removed satisfactorily. Modern dishwashing agents, in particular automatic dishwashing agents, often do not meet the requirements with regard to removing such stains. There is therefore still a need for dishwashing agents, including in particular automatic dishwashing agents which reliably remove protein-containing and bleachable stains, in particular even at lower cleaning temperatures.

In this regard, European patent application EP0846155 discloses that the addition of lipase increases the effect of bleaches on tea stains. The use of amino acids as bleach stabilizers emerges from European patent application EP0476257.

The objective is to further improve the cleaning performance of dishwashing agents, in particular the cleaning performance on protein-containing and/or bleachable stains, in particular tea stains.

In general, only selected proteases are suitable for use in liquid, tenside-containing preparations in any case. Many proteases do not exhibit sufficient catalytic performance in such preparations. For the use of proteases in cleaning agents, therefore, a high catalytic activity and stability under conditions as they are during a wash cycle is particularly desirable.

SUMMARY

The objective is therefore in a first aspect a dishwashing agent comprising a hydrogen peroxide source, a bleach catalyst and a *Bacillus gibsonii* protease, which comprises an amino acid sequence which has at least 70% sequence identity with the amino acid sequence given in SEQ ID NO: 1 over its entire length and which has an amino acid substitution on at least one of the positions corresponding to positions 12, 43, 122, 127, 154, 156, 160, 211, 212 and 222, relating in each case to the numbering according to SEQ ID NO: 1.

A further objective is a dishwashing agent comprising a hydrogen peroxide source, a bleach catalyst and a *Bacillus gibsonii* protease which has at least 70% sequence identity with the amino acid sequence given in SEQ ID NO: 1 over its entire length and which has at least one of the amino acid substitutions Q12L, 143V, M122L, D127P, N154S, T156A, G160S, M211N, M211L, P212D, P212H or A222S on at least one of the positions corresponding to positions 12, 43, 122, 127, 154, 156, 160, 211, 212 and 222, based in each case on the numbering according to SEQ ID NO: 1.

Another objective is a method for producing such a dishwashing agent and a method for removing protein-containing stains, in particular egg stains, and/or bleachable stains, in particular tea stains, on hard surfaces, in particular dishware.

Another objective is a use of such a dishwashing agent for cleaning hard surfaces, in particular dishware, in particular for removing protein-containing stains, in particular egg stains, and/or bleachable soiling, in particular tea stains.

These and other aspects, features and advantages will become apparent to a person skilled in the art through the study of the following detailed description and claims. Any feature from one aspect can be used in any other aspect. Furthermore, it will readily be understood that the examples contained herein are intended to describe and illustrate but not to limit the invention and that, in particular, the invention is not limited to these examples.

DETAILED DESCRIPTION

Unless indicated otherwise, all percentages are indicated in terms of wt. %. Numerical ranges that are indicated in the format "from x to y" also include the stated values. If several preferred numerical ranges are indicated in this format, it is readily understood that all ranges that result from the combination of the various endpoints are also included. "At least one," as used herein, means one or more, i.e. 1, 2, 3, 4, 5, 6, 7, 8, 9, 10, 11, 12, 13, 14 or more. The term "dishwashing agent," as used herein, is synonymous with the term "cleaning agent" or "agent" and denotes a composition for cleaning hard surfaces, in particular dishes, as explained in the description. "About," "approx." or "approximately," as used herein in relation to a numerical value, relates to the corresponding numerical value±10%, preferably ±5%.

Dishwashing agents may include proteases which comprise an amino acid sequence which has at least 70% sequence identity to the amino acid sequence given in SEQ ID NO: 1 over its entire length and at least one amino acid substitution on at least one of the positions that correspond to positions 12, 43, 122, 127, 154, 156, 160, 211, 212 and 222, each based on the numbering according to SEQ ID NO: 1, not only have an improved cleaning performance on protein-containing stains, in particular egg stains, but also in combination with a bleach catalyst, have a very good bleaching performance and consequently show a very good cleaning performance on bleachable stains, in particular tea stains.

This is particularly surprising insofar as no such *Bacillus gibsonii* protease has hitherto been associated with improved cleaning performance in dishwashing agents, in particular not with regard to protein-containing and bleachable stains. In particular, the very good cleaning performance on bleachable stains is remarkable, since proteases are generally sensitive to bleaching agents in detergents and cleaning agents and do not work well in the presence of bleaching agents. The proteases not only seem to be less sensitive to bleaching agents in the cleaning agent and thus show a generally improved cleaning performance on protein-containing stains, but in preferred embodiments of the agents there is also a synergism between the corresponding protease and the bleaching catalyst with regard to cleaning performance, in particular with regard to cleaning performance on tea stains.

Further preferred embodiments of agents show such advantageous cleaning performances even at low temperatures and/or with short wash cycles. A low temperature is preferably between 10 and 50° C., preferably between 15 and 45° C. and particularly preferably between 20 and 40° C. A short rinse cycle preferably lasts a maximum of 60 minutes, 45 minutes or only a maximum of 30 minutes. Further preferred embodiments of agents also show an improved final rinse performance.

The cleaning performance describes the ability of a dishwashing agent, in particular an automatic dishwashing detergent, to partially or completely remove existing stains. Both the dishwashing agent, which comprises the protease or the cleaning liquor formed by this agent, and the protease itself have a respective cleaning performance. The cleaning performance of the enzyme thus contributes to the cleaning performance of the agent or the cleaning liquor formed by the agent.

The cleaning liquor is understood to mean that use solution containing the dishwashing agent which acts on the hard surfaces and thus comes into contact with the stains present on the hard surfaces. The cleaning liquor is usually created when the cleaning process begins and the dishwashing agent is diluted with water, for example in a dishwasher or in another suitable container.

The cleaning performance can be determined in a system that contains an automatic dishwashing agent in a dosage as specified herein and the protease, wherein the proteases to be compared are used in the same concentration (based on active protein) and the cleaning performance against stains of tea, meat, spaghetti, egg and/or creme brûlée is determined according to the IKW method in a Miele GSL (program 45° C., 21° dH). The concentration of the protease in the washing agent intended for this washing system is 0.001 to 0.1 wt. %, preferably 0.01 to 0.06 wt. % based on active, purified protein.

A reference agent for such a washing system can be composed as follows:

|  | Wt. % |
| --- | --- |
| Citrate, Na salt | 15-20 |
| Phosphonate (e.g. HEDP) | 0-7.5 |
| If permitted by the regulations | (2.5-7.5) |
| MGDA, Na salt | 0-25 |
| Disilicate, Na salt | 5-35 |
| Soda | 10-25 |
| Silver protection | 0.0-1.0 |
| Percarbonate, Na salt | 10-15 |
| Bleach catalyst (preferably Mn-based) | 0.02-0.5 |
| Bleach activator (e.g. TAED) | 1-3 |
| Non-ionic tenside(s), e.g. fatty alcohol alkoxylate, preferably 20-40 EO, optionally end-capped | 2.5-10 |
| Polycarboxylate | 4-10 |
| Cationic copolymer | 0-0.75 |
| Disintegrant - (e.g. crosslinked PVP) | 0-1.5 |
| Protease preparation (tq) | 0-5 |
| Amylase preparation (tq) | 0-3 |
| Perfume | 0.05-0.25 |
| Dye solution | 0.0-1 |
| Zinc salt | 0.1-0.3 |
| Sodium sulfate | 0.0-10 |
| Water | 0.0-1.5 |
| pH adjuster (e.g. citric acid) | 0-1.5 |
| Processing aids | 0-5 |

The activity-equivalent use of the relevant protease ensures that the respective enzymatic properties, for example the cleaning performance on certain stains, are compared even if the ratio of active substance to total protein (the values of the specific activity) diverges. In general, a low specific activity can be compensated for by adding a larger amount of protein. Furthermore, the enzymes to be examined can also be used in the same amount of substance or amount by weight if the enzymes to be examined have a different affinity for the test substrate in an activity test. The expression "same amount of substance" in this context relates to a molar use of the enzymes to be investigated. The term "equal weight" relates to the use of the same weight of the enzymes to be investigated.

Otherwise, methods for determining protease activity are well known to, and routinely used by, a person skilled in the art of enzyme technology. For example, such methods are disclosed in Tenside, vol. 7 (1970), pp. 125-132. The protease activity is usually indicated in protease units (PU). Suitable protease activities are, for example, 2.25, 5 or 10 PU per mL of washing liquor or washing process. However, the protease activity is not equal to zero.

The protein concentration can be determined using known methods, for example the BCA method (bicinchoninic acid; 2,2'-bichinolyl-4,4'-dicarboxylic acid) or the Biuret method (Gornall et al., 1948, J. Biol. Chem., 177: 751-766). The active protein concentration can be determined in this regard by titrating the active centers using a suitable irreversible inhibitor and determining the residual activity (cf. M. Bender et al., 1966, J. Am. Chem. Soc. 88 (24): 5890-5913).

The proteases exhibit enzymatic activity, i.e. they are capable of hydrolyzing peptides and proteins, in particular in a detergent or cleaning agent. A protease is therefore an enzyme which catalyzes the hydrolysis of amide/peptide bonds in protein/peptide substrates and is thus able to cleave proteins or peptides. Furthermore, a protease is preferably a mature protease, i.e. the catalytically active molecule without signal peptide(s) and/or propeptide(s). Unless stated otherwise, the sequences given also each refer to mature (processed) enzymes.

In various embodiments, the protease is a free enzyme. This means that the protease can act directly with all the components of an agent and, if the agent is a liquid agent, that the protease is in direct contact with the solvent of the agent (e.g. water). In other embodiments, an agent may contain proteases that form an interaction complex with other molecules or that contain a "coating." In this case, an individual protease molecule or multiple protease molecules may be separated from the other constituents of the agent by a surrounding structure. Such a separating structure may arise from, but is not limited to, vesicles such as a micelle or a liposome. The surrounding structure may also be a virus particle, a bacterial cell or a eukaryotic cell. In various embodiments, an agent may include cells of *Bacillus gibsonii* or *Bacillus subtilis* which express the proteases, or cell culture supernatants of such cells.

Surprisingly, it is precisely those proteases which comprise an amino acid sequence which has at least 70% sequence identity to the amino acid sequence given in SEQ ID NO: 1 over its entire length and an amino acid substitution on at least one of the positions corresponding to positions 12, 43, 122, 127, 154, 156, 160, 211, 212 and 222, each based on the numbering according to SEQ ID NO: 1, which in dishwashing agents on the one hand improve the cleaning performance on protein-containing stains, in particular egg stains, and on the other hand in the interaction with the bleach catalyst in an agent bring about an improved cleaning performance on bleachable stains, in particular tea stains. In this regard, there is preferably a synergistic interaction.

Furthermore, in various embodiments, the *Bacillus gibsonii* protease contains at least one amino acid substitution selected from the group consisting of Q12L, I43V, M122L, D127P, N154S, T156A, G160S, M211N, M211L, P212D, P212H or A222S, in each case based on the numbering according to SEQ ID NO:1.

In further preferred embodiments, the protease used contains one of the following amino acid substitution variants: (i) I43V; (ii) M122L, N154S, and T156A; (iii) M211N and P212D; (iv) M211L and P212D; (v) G160S; (vi) D127P, M211L and P212D; (vii) P212H; or (viii) Q12L, M122L and A222S, wherein the numbering in each case is based on the numbering according to SEQ ID NO: 1.

In further embodiments, the protease used comprises an amino acid sequence which, over its entire length, is preferably at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence given in SEQ ID NO:1, and, in each case based on the numbering according to SEQ ID NO:1, comprises (a) one or more amino acid substitutions 12L, 43V, 122L, 127P, 154S, 156A, 160S, 211N, 211L, 212D, 212H or 222S corresponding to the positions 12, 43, 122, 127, 154, 156, 160, 211, 212 or 222 in the numbering according to SEQ ID NO:1.

The protease may include the stated substitutions means that it contains at least one of the corresponding amino acids in the corresponding positions, i.e. not all of the 10 positions are otherwise mutated or deleted, for example by fragmentation of the protease.

The identity of nucleic acid or amino acid sequences is determined by a sequence comparison. This sequence comparison is based on the BLAST algorithm established and commonly used in the prior art (cf. e.g. Altschul et al. (1990) "Basic local alignment search tool," J. Mol. Biol. 215:403-410, and Altschul et al. (1997): "Gapped BLAST and PSI-BLAST: a new generation of protein database search programs," Nucleic Acids Res., 25:3389-3402) and occurs in principle by similar sequences of nucleotides or amino acids in the nucleic acid or amino acid sequences being assigned to one another. The assignment of the relevant positions shown in a table is referred to as an alignment. Another algorithm available in the prior art is the FASTA algorithm. Sequence comparisons (alignments), in particular multiple sequence comparisons, are created using computer programs. The Clustal series (cf. e.g. Chenna et al. (2003) "Multiple sequence alignment with the Clustal series of programs," Nucleic Acid Res. 31: 3497-3500), T-Coffee (cf. e.g. Notredame et al. (2000) "T-Coffee: A novel method for multiple sequence alignments," J. Mol. Biol. 302:205-217) or programs based on these programs or algorithms, for example, are frequently used. Sequence comparisons (alignments) using the computer program Vector NTI® Suite 10.3 (Invitrogen Corporation, 1600 Faraday Avenue, Carlsbad, California, USA) with the predetermined, default parameters, and the AlignX module of which for sequence comparisons is based on ClustalW, are also possible. Unless stated otherwise, the sequence identity given herein is determined by the BLAST algorithm.

Such a comparison also allows conclusions to be drawn regarding the similarity of the compared sequences. It is usually given in percent identity, i.e. the proportion of identical nucleotides or amino acid radicals in said sequences or in an alignment of corresponding positions. The broader concept of homology takes conserved amino acid exchanges into account in the case of amino acid sequences, i.e. amino acids having similar chemical activity, since they usually perform similar chemical activities within the protein. Therefore, the similarity of the compared sequences may also be stated as percent homology or percent similarity. Identity and/or homology information can be provided regarding whole polypeptides or genes or only regarding individual regions. Homologous or identical regions of different nucleic acid or amino acid sequences are therefore defined by matches in the sequences. Such regions often comprise identical functions. They can be small and comprise only a few nucleotides or amino acids. Often, such small regions perform essential functions for the overall activity of the protein. It may therefore be expedient to relate sequence matches only to individual, optionally small regions. Unless stated otherwise, however, identity or homology information in the present application relates to the entire length of the particular nucleic acid or amino acid sequence indicated. The indication that an amino acid position corresponds to a numerically designated position in SEQ ID NO:1 therefore means that the corresponding position is associated with the numerically designated position in SEQ ID NO:1 in an alignment as defined above.

A cleaning agent with a protease can be obtained from a protease as the starting molecule by one or more conservative amino acid substitutions. The term "conservative amino acid substitution" means the exchange (substitution) of one amino acid radical for another amino acid radical, with this exchange not resulting in a change to the polarity or charge at the position of the exchanged amino acid, e.g. the exchange of a nonpolar amino acid radical for another nonpolar amino acid radical. Conservative amino acid substitutions include, for example: G=A=S, I=V=L=M, D=E, N=Q, K=R, Y=F, S=T, G=A=I=V=L=M=Y=F=W=P=S=T.

A cleaning agent with a protease can be obtained from a protease as a starting molecule by fragmentation, deletion, insertion or substitution mutagenesis and comprises an amino acid sequence which matches the starting molecule over a length of at least 50, 60, 70, 80, 90, 100, 110, 120, 130, 140, 150, 160, 170, 180, 190, 200, 210, 220, 230, 240, 250, 260, 261, 262, 263, 264, 265, 266, 267, 268 or 269 contiguous amino acids.

For instance, it is possible to delete individual amino acids at the termini or in the loops of the enzyme without the proteolytic activity being lost or diminished in the process. Furthermore, such fragmentation or deletion, insertion or substitution mutagenesis can also e.g. reduce the allergenicity of the enzymes concerned and thus improve their overall applicability. The enzymes advantageously retain their proteolytic activity even after the mutagenesis, i.e. their proteolytic activity corresponds at least to that of the starting enzyme. Other substitutions can also exhibit advantageous effects. Both single and multiple contiguous amino acids can be exchanged for other amino acids.

A protease can additionally be stabilized, in particular by one or more mutations, for example substitutions, or by coupling to a polymer. An increase in stability during storage and/or during use, for example in the washing process, leads to longer enzymatic activity and thus improves the cleaning performance. In principle, all stabilization options which are described in the prior art and/or are appropriate are considered. Those stabilizations are preferred which are achieved by mutations of the enzyme itself, since such stabilizations do not require any further work steps following the recovery of the enzyme. Further possibilities for stabilization are, e.g.:

altering the binding of metal ions, in particular the calcium binding sites, for example by exchanging one or more of the amino acid(s) that are involved in the calcium binding with one or more negatively charged amino acids and/or by introducing sequence alterations in at least one of the sequences of the two amino acids arginine and glycine;

protecting against the influence of more denaturing agents such as tensides by mutations that cause an alteration of the amino acid sequence on or at the surface of the protein;

exchanging amino acids near the N-terminus with those likely to contact the rest of the molecule via non-covalent interactions, thus contributing to the maintenance of the globular structure.

Preferred embodiments are those in which the enzyme is stabilized in several ways, as several stabilizing mutations act additively or synergistically.

The protease as described above may have at least one chemical modification. A protease with such an alteration is referred to as a derivative, i.e. the protease is derivatized. In the context of the present application, derivatives are thus understood to mean those proteins of which the pure amino acid chain has been chemically modified. Such derivatizations can be achieved, e.g., in vivo by the host cell that expresses the protein. In this regard, couplings of low-molecular-weight compounds such as lipids or oligosaccharides are particularly noteworthy. However, the derivatizations may also be carried out in vitro, for example by the chemical conversion of a side chain of an amino acid or by covalent bonding of another compound to the protein. For example, it is possible to couple amines to carboxyl groups of an enzyme in order to alter the isoelectric point. Another such compound may also be another protein that is bound to a protein via bifunctional chemical compounds, for example. Derivatization is also understood to mean the covalent bonding to a macromolecular carrier or a non-covalent inclusion in suitable macromolecular cage structures. Derivatizations may, e.g., affect the substrate specificity or bonding strength to the substrate or cause a temporary blockage of the enzymatic activity when the coupled substance is an inhibitor. This can be expedient, e.g., for the period of storage. Such modifications may further affect the stability or enzymatic activity. They can also be used to reduce the allergenicity and/or immunogenicity of the protein and thus, e.g., increase its skin compatibility. For example, couplings with macromolecular compounds, for example polyethylene glycol, can improve the protein in terms of stability and/or skin compatibility. Derivatives of a protein can also be understood in the broadest sense to mean preparations of these proteins. Depending on the recovery, processing or preparation, a protein can be socialized with various other substances, e.g. from the culture of the producing microorganisms. A protein may also have been deliberately added to other substances, e.g. to increase its storage stability. This is also irrespective of whether or not it actually exhibits this enzymatic activity in a particular preparation. This is because it may be desired that it has no or only low activity during storage and exhibits its enzymatic function only at the time of use. This can be controlled via appropriate accompanying substances, for example.

Numerous proteases and in particular subtilisins are formed as so-called preproteins, i.e. together with a propeptide and a signal peptide, wherein the function of the signal peptide usually is to ensure the release of the protease from the cell producing it into the periplasm or the medium surrounding the cell, and the propeptide is usually necessary for the protease to fold correctly. The signal peptide and the propeptide are usually the N-terminal part of the preprotein. The signal peptide is split off from the rest of the protease under natural conditions by a signal peptidase. The correct final folding of the protease, supported by the propeptide, then takes place. The protease is then in its active form and cleaves the propeptide itself. After the propeptide has been split off, the then-mature protease, in particular subtilisin, exerts its catalytic activity without the N-terminal amino acids originally present. For technical applications in general, the mature proteases, i.e. the enzymes processed after their production, are preferred over the preproteins. The proteases can also be modified by the cells producing them after the production of the polypeptide chain, for example by attaching sugar molecules, formylations, aminations, etc. Such modifications are post-translational modifications and can, but do not have to, have an influence on the function of the protease.

"Variant," as used herein, relates to naturally or artificially generated variations of a native protease which has an amino acid sequence which is modified from the reference form. In addition to the amino acid alterations discussed above, proteases can have other amino acid alterations, in particular amino acid substitutions, insertions or deletions. Such proteases are, e.g., developed by targeted genetic alteration, i.e. by mutagenesis methods, and optimized for specific applications or with regard to specific properties (e.g. with regard to their catalytic activity, stability, etc.). Furthermore, nucleic acids can be introduced into recombination approaches and can thus be used to generate completely new types of proteases or other polypeptides. The aim is to introduce targeted mutations such as substitutions, insertions or deletions into the known molecules in order, e.g., to improve the cleaning performance of enzymes. For this purpose, in particular the surface charges and/or the isoelectric point of the molecules and thus their interactions with the substrate can be altered. For instance, the net charge of the enzymes can be altered in order to influence the substrate binding, in particular for use in detergents and cleaning agents. Alternatively or additionally, one or more corresponding mutations can increase the stability or catalytic activity of the enzyme and thus improve its cleaning performance. Advantageous properties of individual mutations, e.g. individual substitutions, can complement one another. A protease that has already been optimized with regard to certain properties can therefore be further developed, for example with regard to its stability towards tensides and/or bleaches and/or other components.

For the description of substitutions relating to exactly one amino acid position (amino acid exchanges), the following convention is used herein: first, the naturally occurring amino acid is designated in the form of the internationally used one-letter code, followed by the associated sequence position and finally the inserted amino acid. Several exchanges within the same polypeptide chain are separated by slashes. For insertions, additional amino acids are named following the sequence position. In the case of deletions, the missing amino acid is replaced by a symbol, e.g. a star or a dash, or a Δ is indicated before the corresponding position. For example, P14H describes the substitution of proline at position 14 by histidine, P14HT the insertion of threonine after the amino acid histidine at position 14 and P14* or ΔP14 the deletion of proline at position 14. This nomenclature is known to a person skilled in the field of enzyme technology.

The amino acid positions are in this case defined by an alignment of the amino acid sequence of a protease with the amino acid sequence of the protease from *Bacillus gibsonii*, as given in SEQ ID NO:1. Furthermore, the assignment of the positions depends on the mature protein. This assignment is also to be used in particular if the amino acid sequence of a protease comprises a higher number of amino acid radicals than the protease from *Bacillus gibsonii* according to SEQ ID NO:1. Proceeding from the above-mentioned positions in the amino acid sequence of the protease from *Bacillus gibsonii*, the alteration positions in a protease used are those which are assigned to precisely these positions in an alignment.

In a further embodiment, the protease is characterized in that the cleaning performance thereof is not significantly reduced compared with that of a protease comprising an amino acid sequence that corresponds to the amino acid sequence given in SEQ ID NO:1, i.e. has at least 80% of the reference washing performance, preferably at least 100%, more preferably at least 110% or more. The cleaning performance can be determined as described above.

A dishwashing agent increasingly preferably contains the protease in an amount of $1 \times 10^{-8}$ to 10 wt. %, 0.00001 to 2 wt. %, 0.001 to 1 wt. %, 0.007 to 0.8 wt. %, 0.025 to 0.5 wt. % and particularly preferably from 0.04 to 0.38 wt. %, based on the active protein content of the protease.

A dishwashing agent also comprises a bleach activator. These substances are preferably bleach-intensifying transition metal salts or transition metal complexes such as Mn, Fe, Co, Ru or Mo salen complexes or carbonyl complexes. Mn-, Fe-, Co-, Ru-, Mo-, Ti-, V-, and Cu-complexes with N-containing tripod ligands as well as Co-, Fe- Cu-, and Ru-ammine complexes can also be used as bleach catalysts.

Complexes of manganese in oxidation stage II, III, IV, or IV are particularly preferably used which preferably contain one or more macrocyclic ligands with the donor functions N, NR, PR, 0 and/or S. Preferably, ligands are used which have nitrogen donor functions. It is particularly preferred to use bleach catalyst(s) in the agents which contain, as macromolecular ligands, 1,4,7-trimethyl-1,4,7-triazacyclononane (Me-TACN), 1,4,7-triazacyclononane (TACN), 1,5,9-trimethyl-1,5,9-triazacyclododecane (Me-TACD), 2-methyl-1,4,7-trimethyl-1,4,7-triazacyclononane (Me/Me-TACN), and/or 2-methyl-1,4,7-triazacyclononane (Me/TACN). Suitable manganese complexes are, for example $[Mn^{III}_2 \, (\mu\text{-}O)_1(\mu\text{-}OAc)_2(TACN)_2](ClO_4)_2$, $[Mn^{III} \, Mn^{IV} \, (\mu\text{-}O)_2(\mu\text{-}OAc)_1(TACN)_2](BPh_4)_2$, $[Mn^{IV}_4 \quad (\mu\text{-}O)_6(TACN)_4](ClO_4)_4$, $[Mn^{III}Mn^{IV}(\mu\text{-}O)_2(\mu\text{-}OAc)_2(Me\text{-}TACN)_2](ClO_4)_2$, $[Mn^{III}Mn^{IV}(\mu\text{-}O)_1(\mu\text{-}OAc)_2(Me\text{-}TACN)_2](ClO_4)_3$, $[Mn^{IV}_2 \, (\mu\text{-}O)_3(Me\text{-}TACN)_2](PF_6)_2$ and $[Mn^{IV}_2 \, (\mu\text{-}O)_3(Me/Me\text{-}TACN)_2](PF_6)_2(OAc=OC(O)CH_3)$.

Dishwashing agents, in particular automatic dishwashing detergents, characterized in that they contain a bleach catalyst selected from the group of the bleach-intensifying transition metal salts and transition metal complexes, preferably from the group of the complexes of manganese with 1,4,7-trimethyl-1,4,7-triazacyclononane (Me-TACN) or 1,2, 4,7-tetramethyl-1,4,7-triazacyclononane (Me/Me-TACN) are preferred, since the aforementioned bleach catalysts in particular can significantly improve the cleaning result.

The aforementioned bleach-intensifying transition metal complexes, in particular with the central atoms Mn and Co, are preferably used in an amount of up to 5 wt. %, in particular 0.0025 to 1 wt. % and particularly preferably 0.01 to 0.30 wt. %, in each case based on the total weight of the bleach catalyst-containing compositions. In special cases, however, more bleach catalyst can also be used.

A dishwashing agent further comprises a source of hydrogen peroxide. These are compounds that deliver or can deliver $H_2O_2$ in water. The hydrogen peroxide source is preferably a bleaching agent, wherein oxygen bleaching agents are preferred.

From the group of compounds which act as bleaching agents and yield $H_2O_2$ in water, sodium percarbonate, sodium perborate tetrahydrate and sodium perborate monohydrate are of particular significance. Further examples of bleaching agents which may be used are peroxypyrophosphates, citrate perhydrates as well as $H_2O_2$-yielding peracid salts or peracids, such as perbenzoates, peroxophthalates, diperazelaic acid, phthaloiminoperacid or diperdodecane diacid.

Moreover, bleaching agents from the group of the organic bleaching agents can also be used. Typical organic bleaching agents are diacyl peroxides such as dibenzoyl peroxide.

Other typical organic bleaching agents are the peroxy acids, with the alkylperoxy acids and the arylperoxy acids meriting special mention as examples.

The hydrogen peroxide source is preferably contained in the dishwashing agent in an amount of 2 to 30 wt. % and increasingly preferably 4 to 25 wt. %, 5 to 20 wt. % and particularly preferably 6 to 15 wt. %, respectively based on the total weight of the dishwashing detergent. Preferred dishwashing agent are also characterized in that the dishwashing agent, in each case based on the total weight of the automatic dishwashing detergent, contains 2 to 20 wt. %, preferably 3 to 18 wt. % and in particular 4 to 15 wt. % sodium percarbonate.

Particularly preferred embodiments of dishwashing agents are consequently characterized in that the bleach catalyst is selected from the group of the bleach-enhancing transition metal salts and transition metal complexes, preferably from the group of the complexes of manganese with 1,4,7-trimethyl-1,4,7-triazacyclononane (Me-TACN) or 1,2,4,7-tetramethyl-1,4,7-triazacyclononane (Me/Me-TACN), and/or the hydrogen peroxide source is sodium percarbonate, sodium perborate tetrahydrate or sodium perborate monohydrate or a combination thereof. The bleach catalyst is very particularly preferably a complex of manganese with 1,4,7-trimethyl-1,4,7-triazacyclononane (Me-TACN), in particular $[Mn^{IV}_2 (\mu\text{-}O)_3(Me\text{-}TACN)_2](PF_6)_2$, or 1,2,4,7-tetramethyl-1,4,7-triazacyclononane (Me/Me-TACN) or a mixture thereof, and the hydrogen peroxide source sodium percarbonate. The bleach catalyst and the hydrogen peroxide source are preferably present in the abovementioned amounts in the combinations mentioned.

Dishwashing agents, in particular automatic dishwashing agents, can also contain bleach activators, for example in order to achieve an improved bleaching effect when cleaning at temperatures of 60° C. and below. Compounds which, under perhydrolysis conditions, result in aliphatic peroxocarboxylic acids having preferably 1 to 10 C atoms, in particular 2 to 4 C atoms, and/or optionally substituted perbenzoic acid, may be used as bleach activators. Substances that have O acyl and/or N acyl groups of the stated number of C atoms and/or optionally substituted benzoyl groups are suitable. Multiply acylated alkylene diamines are preferred, with tetraacetylethyl ethylenediamine (TAED) having proven to be particularly suitable.

These bleach activators are preferably used in amounts of 0.1 to 10 wt. %, in particular 0.1 to 8 wt. %, especially 2 to 8 wt. % and particularly preferably 2 to 6 wt. %, based in each case on the total weight of the agent.

In a preferred embodiment, a dishwashing agent is an automatic dishwashing agent. In terms of the present application, automatic dishwashing agents are compositions that can be used to clean soiled dishes in an automatic dishwashing process. The automatic dishwashing agents thus differ from automatic rinse aids, which are always used in combination with automatic dishwashing agents and do not have any cleaning effect of their own.

Machine-washed dishes are often subject to higher requirements than manually washed dishes. After machine cleaning, the dishes should not only be free of food residues, but should also not have any whitish stains due to water hardness or other mineral salts, which come from dried water droplets due to the lack of wetting agents. Modern machine dishwashing agents meet these requirements by integrating cleaning and/or maintaining and/or water-softening and/or rinsing active ingredients and are known to consumers as "2in1" or "3in1" dishwashing agents, for example. Automatic dishwashing agents contain builders as an essential component for cleaning and rinsing success. On the one hand, these builders increase the alkalinity of the cleaning liquor, wherein fats and oils are emulsified and saponified with increasing alkalinity, and on the other hand, by complexing the calcium ions contained in the aqueous liquor, they reduce the water hardness of the cleaning liquor.

The dishwashing agent can furthermore comprise at least one further ingredient selected from the group consisting of tensides, builders, (anionic) polymers, glass corrosion inhibitors, corrosion inhibitors and combinations thereof. They may also contain water-miscible organic solvents, further enzymes, sequestering agents, electrolytes, pH regulators and/or further auxiliaries such as optical brighteners, graying inhibitors, color-transferring inhibitors, foam regulators, as well as dyes and fragrances, and combinations thereof. In a further embodiment, a dishwashing agent is phosphate-free. Phosphate-free dishwashing agents are particularly advantageous from an environmental point of view.

The ingredients of the agents are preferably matched to one another. Synergies with regard to the cleaning performance and/or the rinsing performance and/or the deposit inhibition are preferred. Synergies which are present in a temperature range between 10 and 100° C., in particular in a temperature range from 15 to 100° C., 20 to 70° C., 20 to 60° C., 20 to 50° C., 20 to 40° C., 15 to 30° C. and 15 to 25° C. are particularly preferred.

Dishwashing agents, in particular automatic dishwashing agents, can contain one or more tensides, wherein anionic tensides, nonionic tensides and mixtures thereof are particularly suitable.

Preferred among the anionic tensides are those which have at least one sulfate or sulfonate group. The anionic tenside with at least one sulfate or sulfonate group is preferably selected from fatty alcohol sulfates, alkane sulfonates and alkylbenzenesulfonates. Preferred here are C12-18 fatty alcohol sulfates (FAS), for example Sulfopon K 35 (Cognis, Germany), secondary C13-17 alkanesulfonates (SAS), for example Hostapur SAS 93 (Clariant, Germany), and linear C8-18 alkylbenzenesulfonates, especially dodecylbenzenesulfonate (LAS). The terms "sulfate" and "sulfonate" include not only relevant anionic compounds which are present in the form of salts, but also the free acids, that is to say the corresponding alkylsulfuric acids or alkylsulfonic acids. The anionic tenside with at least one sulfate or sulfonate group in dishwashing agents is preferably contained in an amount from 0.1 to 20 wt. %, particularly preferably from 0.5 to 15 wt. %, in particular from 2.5 to 10 wt. %.

The non-ionic tensides are a preferred component of the cleaning agent, wherein nonionic tensides of the general formula $R^1\text{—}CH(OH)CH_2O\text{-}(AO)_w\text{-}(A'O)_x\text{-}(A''O)_y\text{-}(A'''O)_z\text{—}R^2$, in which $R^1$ represents a straight-chain or branched, saturated or mono- or polyunsaturated $C_{6-24}$-alkyl or -alkenyl radical; $R^2$ represents a linear or branched hydrocarbon radical having 2 to 26 carbon atoms; A, A', A'' and A''' independently of one another represent a radical from the group $—CH_2CH_2$, $—CH_2CH_2—CH_2$, $—CH_2—CH(CH_3)$, $—CH_2—CH_2—CH_2—CH_2$, $—CH_2—CH(CH_3)—CH_2—$, $—CH_2—CH(CH_2—CH_3)$, and w, x, y and z represent values between 0.5 and 120, wherein x, y and/or z can also be 0, are preferred.

By adding the abovementioned non-ionic tensides of the general formula $R^1\text{—}CH(OH)CH_2O\text{-}(AO)_w\text{-}(A'O)_x\text{-}(A''O)_y\text{-}(A'''O)_z\text{—}R^2$, subsequently also referred to as "hydroxy mixed ethers," the cleaning performance of enzyme-containing preparations can surprisingly be significantly improved, both in comparison with tenside-free systems and in comparison with systems containing alternative non-ionic tensides, for example from the group of poly-alkoxylated fatty alcohols.

By using these non-ionic tensides having one or more free hydroxyl group(s) on one or both terminal alkyl radicals, the stability of the enzymes contained in the cleaning agent preparations can be improved substantially.

Particularly preferred are end-capped poly(oxyalkylated) non-ionic tensides which, according to the formula $R^1O[CH_2CH_2O]_xCH_2CH(OH)R^2$, also comprise, in addition to a radical $R^1$, which represents linear or branched, saturated or unsaturated, aliphatic or aromatic hydrocarbon radicals having 2 to 30 carbon atoms, preferably having 4 to 22 carbon atoms, a linear or branched, saturated or unsaturated, aliphatic or aromatic hydrocarbon radical $R^2$ having 1 to 30 carbon atoms, wherein x represents values between 1 and 90, preferably values between 30 and 80, and in particular values between 30 and 60.

Tensides of the formula $R^1O[CH_2CH(CH_3)O]_x$ $[CH_2CH_2O]_yCH_2CH(OH)R^2$ are particularly preferred, in which $R^1$ represents a linear or branched aliphatic hydrocarbon radical having 4 to 18 carbon atoms or mixtures thereof, $R^2$ represents a linear or branched hydrocarbon radical having 2 to 26 carbon atoms or mixtures thereof, and x represents values between 0.5 and 1.5, and y represents a value of at least 15. The group of these non-ionic tensides includes, e.g., the $C_{2-26}$ fatty alcohol-$(PO)_1$-$(EO)_{15-40}$-2-hydroxyalkyl ethers, in particular also the $C_{8-10}$ fatty alcohol-$(PO)_1$-$(EO)_{22}$-2-hydroxydecyl ethers.

Particularly preferred are also end-capped poly(oxyalkylated) non-ionic tensides of the formula $R^1O[CH_2CH_2O]_x$ $[CH_2CH(R_3)O]_yCH_2CH(OH)R^2$, in which $R^1$ and $R^2$, independently of one another, represent a linear or branched, saturated or mono- or polyunsaturated hydrocarbon radical having 2 to 26 carbon atoms, $R^3$ is selected, independently of one another, from $—CH_3$, $—CH_2CH_3$, $—CH_2CH_2—CH_3$, $—CH(CH_3)_2$, but preferably represents $—CH_3$, and x and y represent, independently of one another, values between 1 and 32, non-ionic tensides having $R^3\!=\!—CH_3$ and values for x of from 15 to 32 and for y of from 0.5 and 1.5 being very particularly preferred.

Further non-ionic tensides that can preferably be used are the end-capped poly(oxyalkylated) non-ionic tensides of the formula $R^1O[CH_2CH(R^3)O]_x[CH_2]_kCH(OH)[CH_2]_jOR^2$, in which $R^1$ and $R^2$ represent linear or branched, saturated or unsaturated, aliphatic or aromatic hydrocarbon radicals having 1 to 30 carbon atoms, $R^3$ represents H or a methyl, ethyl, n-propyl, iso-propyl, n-butyl, 2-butyl or 2-methyl-2-butyl radical, x represents values between 1 and 30, and k and j represent values between 1 and 12, preferably between 1 and 5. If the value x is $\geq 2$, every $R^3$ in the above formula $R^1O[CH_2CH(R^3)O]_x[CH_2]_kCH(OH)[CH_2]_jR^2$ can be different. $R^1$ and $R^2$ are preferably linear or branched, saturated or unsaturated, aliphatic or aromatic hydrocarbon radicals having 6 to 22 carbon atoms, wherein radicals having 8 to 18 C atoms are particularly preferred. For the radical $R^3$, H, $—CH_3$ or $—CH_2CH_3$ are particularly preferred. Particularly preferred values for x are in the range from 1 to 20, in particular from 6 to 15.

As described above, every $R^3$ in the above formula can be different if x≥2. In this way, the alkylene oxide unit in square brackets can be varied. For example, if x represents 3, the radical $R^3$ can be selected in order to form ethylene oxide ($R^3$=H) or propylene oxide ($R^3$=$CH_3$) units, which can be joined together in any sequence, for example (EO)(PO) (EO), (EO)(EO)(PO), (EO)(EO)(EO), (PO)(EO)(PO), (PO) (PO)(EO) and (PO)(PO)(PO). The value 3 for x has been selected here as an example and can by all means be greater, wherein the range of variation increases as the values for x increase and includes a large number of (EO) groups combined with a small number of (PO) groups, e.g., or vice versa.

Particularly preferred end-capped poly(oxyalkylated) alcohols of the above formula have values of k=1 and j=1, and therefore the previous formula is simplified to $R^1O$ $[CH_2CH(R^3)O]_x$ $CH_2CH(OH)CH_2OR^2$. In the aforementioned formula, $R^1$, $R^2$ and $R^3$ are as defined above and x represents numbers from 1 to 30, preferably 1 to 20, and in particular 6 to 18. Tensides in which the radicals $R^1$ and $R^2$ have 9 to 14 C atoms, $R^3$ represents H, and x assumes values from 6 to 15 are particularly preferred.

Finally, the non-ionic tensides of the general formula $R^1$—$CH(OH)CH_2O$-$(AO)_w$—$R^2$, in which $R^1$ represents a straight-chain or branched, saturated or mono- or polyunsaturated $C_{6-24}$-alkyl or -alkenyl radical have proven to be particularly effective; $R^2$ represents a linear or branched hydrocarbon radical having 2 to 26 carbon atoms; A represents a radical from the group —$CH_2CH_2$, —$CH_2CH_2$—$CH_2$, —$CH_2$—$CH(CH_3)$, and w represents values between 1 and 120, preferably 10 to 80, in particular 20 to 40. The group of these non-ionic tensides includes, e.g., $C_{4-22}$ fatty alcohol-$(EO)_{10-80}$-2-hydroxyalkyl ethers, in particular also $C_{8-12}$ fatty alcohol-$(EO)_{22}$-2-hydroxydecyl ethers and $C_{4-22}$ fatty alcohol-$(EO)_{40-80}$-2-hydroxyalkyl ethers.

Preferred cleaning agents are characterized in that the cleaning agent contains at least one non-ionic tenside, preferably a non-ionic tenside from the group of hydroxy mixed ethers, the proportion by weight of the non-ionic tenside with respect to the total weight of the cleaning agent preferably being from 0.2 to 10 wt. %, more preferably from 0.4 to 7.0 wt. % and in particular from 0.6 to 6.0 wt. %.

Preferred cleaning agents for use in automatic dishwashing methods contain, in addition to the non-ionic tensides described above, further tensides, in particular amphoteric tensides. However, the proportion of anionic tensides with respect to the total weight of these cleaning agents is preferably limited. Preferred automatic dishwashing agents are therefore characterized in that they contain less than 5.0 wt. %, preferably less than 3.0 wt. %, particularly preferably less than 2.0 wt. %, of anionic tenside, based on the total weight thereof. Larger quantities of anionic tensides are not used, in particular so as to avoid excessive foaming.

Another preferred component of cleaning agents are complexing agents. Particularly preferred complexing agents are the phosphonates, provided that their use is permitted by regulations. In addition to 1-hydroxyethane-1,1-diphosphonic acid, the complexing phosphonates include a number of different compounds such as diethylenetriamine penta(methylene phosphonic acid) (DTPMP). Hydroxy alkane or amino alkane phosphonates are particularly preferred in this application. Among the hydroxy alkane phosphonates, 1-hydroxyethane-1,1-diphosphonate (HEDP) has particular significance as a cobuilder. It is preferably used as a sodium salt, the disodium salt reacting in a neutral manner and the tetrasodium salt reacting in an alkaline manner (pH 9). Possible amino alkane phosphonates preferably include ethylenediamine tetramethylene phosphonate (EDTMP), diethylenetriamine pentamethylene phosphonate (DTPMP) and the higher homologs thereof. They are preferably used in the form of the neutrally reacting sodium salt, for example as the hexasodium salt of EDTMP or as the hepta- and octa-sodium salt of DTPMP. Of the class of phosphonates, HEDP is preferably used as a builder. The aminoalkane phosphonates additionally have a pronounced heavy-metal-binding power.

Accordingly, it may be preferred, in particular if the agents also contain bleach, to use aminoalkane phosphonates, in particular DTPMP, or to use mixtures of the mentioned phosphonates.

A preferred agent in the context of this application contains one or more phosphonate(s) from the group aminotrimethylene phosphonic acid (ATMP) and/or salts thereof; ethylenediaminetetra (methylenephosphonic acid) (EDTMP) and/or salts thereof; diethylenetriaminepenta (methylenephosphonic acid) (DTPMP) and/or salts thereof; 1-hydroxyethane-1,1-diphosphonic acid (HEDP) and/or its salts; 2-phosphonobutane-1,2,4-tricarboxylic acid (PBTC) and/or salts thereof; hexamethylene diamine tetra (methylene phosphonic acid) (HDTMP) and/or salts thereof; nitrilotri (methylenephosphonic acid) (NTMP) and/or salts thereof.

Particularly preferred cleaning agents are those which contain 1-hydroxyethane-1,1-diphosphonic acid (HEDP) or diethylenetriaminepenta(methylene phosphonic acid) (DTPMP) as phosphonates. The medium may, of course, contain two or more different phosphonates. Cleaning agents that are preferred are characterized in that the cleaning agent contains at least one complexing agent from the group of phosphonates, preferably 1-hydroxyethane-1,1-diphosphonate, wherein the proportion by weight of the phosphonate with respect to the total weight of the cleaning agent preferably is between 0.1 and 8.0 wt. %, more preferably 0.2 and 5.0 wt. % and in particular 0.5 and 3.0 wt. %.

The agents also preferably contain builder. The builders include in particular the silicates and carbonates.

Polycarboxylates/polycarboxylic acids, polymeric polycarboxylates, aspartic acid, polyacetals, dextrins, other organic cobuilders and phosphonates are particularly noteworthy as organic cobuilders. These classes of substances are described below. Organic co-builder substances of this kind can, if desired, be contained in amounts of up to 40 wt. %, in particular up to 25 wt. %, and preferably of 1 wt. % to 8 wt. %.

Organic builders that can be used are the polycarboxylic acids that can be used in the form of the free acids and/or the sodium salts thereof, e.g., wherein polycarboxylic acids are understood to mean those carboxylic acids which carry more than one acid function. For example, these are citric acid, adipic acid, succinic acid, glutaric acid, malic acid, tartaric acid, maleic acid, fumaric acid, saccharic acid, carboxymethyl inulin, monomeric and polymeric aminopolycarboxylic acids, in particular glycinediacetic acid, methylglycinediacetic acid, nitrilotriacetic acid (NTA), iminodisuccinates such as ethylenediamine-N,N'-di succinic acid and hydroxyiminodisuccinate, ethylenediaminetetraacetic acid and polyaspartic acid, polyphosphonic acids, in particular aminotris(methylenephosphonic acid), ethylenediamine tetrakis (methylenephosphonic acid), lysine tetra(methylenephosphonic acid) and 1-hydroxyethane-1,1-diphosphonic acid, polymeric hydroxy compounds such as dextrin, and polymeric (poly)carboxylic acids, polycarboxylates which can be obtained in particular by oxidizing polysaccharides, polymeric acrylic acids, methacrylic acids, maleic acids, and mixed polymers thereof, which may also contain, polymerized in the polymer, small portions of polymerizable substances, without a carboxylic acid functionality. Organic builder substances of this kind can, if desired, be contained in amounts of up to 50 wt. %, in particular up to 25 wt. %, and preferably of 10 wt. % to 20 wt. %.

In addition to their builder effect, the free acids typically also have the property of being an acidification component and are thus also used for setting a lower and milder pH of cleaning agents. Particularly noteworthy here are citric acid, succinic acid, glutaric acid, adipic acid, gluconic acid, and any mixtures thereof. Citric acid or salts of citric acid are particularly preferably used as the builder. Further particularly preferred builder substances are selected from methylglycinediessidic acid (MGDA), glutamic acid diacetate (GLDA), aspartic acid diacetate (ASDA), hydroxyethyliminodiacetate (HEIDA), iminodisuccinate (IDS) and ethylenediamine disuccinate (EDDS), carboxymethyl inulin and polyaspartate.

In preferred embodiments, citric acid and/or citrate is used as the water-soluble, organic builder. It is particularly preferred to use 5 to 25 wt. %, preferably 7.5 to 12.5 wt. % of citric acid and/or 5 to 25 wt. %, preferably 7.5 to 12.5 wt. % citrate, preferably alkali citrate, more preferably sodium citrate. Citric acid/citrate can each be used in the form of their hydrates, for example citric acid can be used in the form of the monohydrate, and citrate can be used in the form of the trisodium citrate dihydrate.

Polymeric polycarboxylates are also suitable as builders. These are, for example, the alkali metal salts of polyacrylic acid or polymethacrylic acid, e.g. those having a relative molecular mass of from 500 to 70,000 g/mol. In the context of this document, the molar masses given for polymeric polycarboxylates are weight-average molar masses $M_W$ of the particular acid form which have been determined in principle using gel permeation chromatography (GPC), wherein a UV detector has been used. The measurement was carried out against an external polyacrylic acid standard which, owing to the structural relationship thereof with the tested polymers, yields realistic molecular weight values. These specifications differ significantly from the molecular weight specifications for which polystyrene sulfonic acids are used as the standard. The molar masses measured against polystyrene sulfonic acids are generally significantly higher than the molar masses specified in this document.

Suitable polymers are in particular polyacrylates which preferably have a molecular mass of from 2,000 to 20,000 g/mol. Due to their superior solubility, the short-chain polyacrylates, which have molar masses of from 2,000 to 10,000 g/mol, and particularly preferably from 3,000 to 5,000 g/mol, may in turn be preferred from this group.

In addition, copolymeric polycarboxylates are suitable, in particular those of acrylic acid with methacrylic acid and those of acrylic acid or methacrylic acid with maleic acid. Copolymers of acrylic acid with maleic acid which contain from 50 wt. % to 90 wt. % acrylic acid and from 50 wt. % to 10 wt. % maleic acid have been found to be particularly suitable. The relative molecular mass thereof, based on free acids, is generally from 2,000 to 70,000 g/mol, preferably from 20,000 to 50,000 g/mol, and in particular from 30,000 to 40,000 g/mol.

In addition to the previously described builders, polymers having a cleaning action can be contained in the cleaning agent. The proportion by weight of the polymers with respect to the total weight of cleaning agents is preferably from 0.1 to 20 wt. %, more preferably from 1.0 to 15 wt. % and in particular from 2.0 to 12 wt. %.

Polymers containing sulfonic acid groups, in particular from the group of copolymeric polysulfonates, are preferably used as polymers having a cleaning action. These copolymeric polysulfonates contain, in addition to sulfonic acid group-containing monomer(s), at least one monomer from the group of unsaturated carboxylic acids.

As unsaturated carboxylic acid(s), unsaturated carboxylic acids of formula $R^1(R^3)COOH$ are particularly preferably used, in which $R^1$ to $R^3$ represent, independently of one another, —H, —CH$_3$, a straight-chain or branched saturated alkyl radical having 2 to 12 carbon atoms, a straight-chain or branched, mono- or polyunsaturated alkenyl radical having 2 to 12 carbon atoms, —NH$_2$, —OH, or —COOH-substituted alkyl or alkenyl radicals as defined above, or represent —COOH or —COOR$^4$, wherein R$^4$ is a saturated or unsaturated, straight-chain or branched hydrocarbon radical having 1 to 12 carbon atoms. Particularly preferred unsaturated carboxylic acids are acrylic acid, methacrylic acid, ethacrylic acid, α-chloroacrylic acid, α-cyanoacrylic acid, crotonic acid, α-phenylacrylic acid, maleic acid, maleic anhydride, fumaric acid, itaconic acid, citraconic acid, methylene malonic acid, sorbic acid, cinnamic acid, or mixtures thereof. Unsaturated dicarboxylic acids can of course also be used.

For sulfonic acid group-containing monomers, those of the formula R$^5$(R$^6$)C=C(R$^7$)—X—SO$_3$H are preferred, in which R$^5$ to R$^7$, independently of one another, represent —H, —CH$_3$, a straight-chain or branched saturated alkyl radical having 2 to 12 carbon atoms, a straight-chain or branched, mono- or polyunsaturated alkenyl radical having 2 to 12 carbon atoms, —NH$_2$, —OH, or —COOH-substituted alkyl or alkenyl radicals, or represent —COOH or —COOR$^4$, where R$^4$ is a saturated or unsaturated, straight-chain or branched hydrocarbon radical having 1 to 12 carbon atoms, and X represents an optionally present spacer group that is selected from —(CH$_2$)$_n$—, where n=0 to 4, —COO—(CH$_2$)$_k$—, where k=1 to 6, —C(O)—NH—C(CH$_3$)$_2$—, —C(O)—NH—C(CH$_3$)$_2$—CH$_2$— and —C(O)—NH—CH(CH$_2$CH$_3$)—.

Among these monomers, those of formulas H$_2$C=CH—X—SO$_3$H, H$_2$C=C(CH$_3$)—X—SO$_3$H and HO$_3$S—X—(R$^6$)C=C(R$^7$)—X—SO$_3$H are preferred, in which R$^6$ and R$^7$, independently of one another, are selected from —H, —CH$_3$, —CH$_2$CH$_3$, —CH$_2$CH$_2$CH$_3$ and —CH(CH$_3$)$_2$, and X represents an optionally present spacer group that is selected from —(CH$_2$)$_n$—, where n=0 to 4, —COO—(CH$_2$)$_k$—, where k=1 to 6, —C(O)—NH—C(CH$_3$)$_2$—, —C(O)—NH—C(CH$_3$)$_2$—CH$_2$— and —C(O)—NH—CH(CH$_2$CH$_3$)—.

Particularly preferred sulfonic acid group-containing monomers are 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxy-propanesulfonic acid, allyl sulfonic acid, methallyl sulfonic acid, allyloxybenzene sulfonic acid, methallyloxybenzene sulfonic acid, 2-hydroxy-3-(2-propenyl oxy)propanesulfonic acid, 2-methyl-2-propene-1-sulfonic acid, styrene sulfonic acid, vinylsulfonic acid, 3-sulfopropyl acrylate, 3-sulfopropyl methacrylate, sulfomethacrylamide, sulfomethylmethacrylamide, as well as mixtures of the above acids or water-soluble salts thereof.

In the polymers, the sulfonic acid groups can be present entirely or partially in neutralized form. The use of partially or fully neutralized sulfonic acid group-containing copolymers is preferred. The molar mass of the sulfo-copolymers that are preferably used can be varied in order to adapt the properties of the polymers to the desired intended use. Preferred automatic dishwashing agents are characterized in that the copolymers have molar masses of 2,000 to 200,000 g/mol, preferably 4,000 to 25,000 g/mol and in particular 5,000 to 15,000 g/mol.

In another preferred embodiment, the copolymers comprise not only carboxyl group-containing monomers and sulfonic acid group-containing monomers but also at least one non-ionic, preferably hydrophobic monomer. In particular the rinsing performance of automatic dishwashing detergents was able to be improved by using these hydrophobically modified polymers.

Dishwashing agents containing a copolymer comprising i) monomer(s) containing carboxylic acid groups, ii) monomer(s) containing sulfonic acid groups, iii) nonionic monomer(s) are preferred. By using these terpolymers, it has been possible to improve the rinsing performance of automatic dishwashing detergents by comparison with comparable dishwashing detergents which contain sulfopolymers without the addition of non-ionic monomers.

As the non-ionic monomers, monomers of the general formula R$^1$(R$^2$)C=C(R$^3$)—X—R$^4$ are preferably used, in which R$^1$ to R$^3$ represent, independently of one another, —H, —CH$_3$ or —C$_2$H$_5$, X represents an optionally present spacer group selected from —CH$_2$—, —C(O)O— and —C(O)—NH—, and R$^4$ represents a straight-chain or branched saturated alkyl radical having 2 to 22 carbon atoms or an unsaturated, preferably aromatic radical having 6 to 22 carbon atoms. Particularly preferred non-ionic monomers are butene, isobutene, pentene, 3-methylbutene, 2-methyl-butene, cyclopentene, hexene, hexene-1, 2-methlypentene-1, 3-methlypentene-1, cyclohexene, methylcyclopentene, cycloheptene, methyl cyclohexene, 2,4,4-trimethylpentene-1, 2,4,4-trimethylpentene-2, 2,3-dimethylhexene-1, 2,4-dimethylhexene-1, 2,5-dimethylhexene-1, 3,5-dimethylhexene-1, 4,4-dimethylhexane-1, ethylcyclohexene, 1-octene, α-olefins having 10 or more carbon atoms such as 1-decene, 1-dodecene, 1-hexadecene, 1-octadecene and C22-α-olefin, 2-styrene, α-methylstyrene, 3-methylstyrene, 4-propyl styrene, 4-cyclohexyl styrene, 4-dodecyl styrene, 2-ethyl-4-benzylstyrene, 1-vinyl naphthalene, 2-vinyl naphthalene, acrylic acid methyl ester, acrylic acid ethyl ester, acrylic acid propyl ester, acrylic acid butyl ester, acrylic acid pentyl ester, acrylic acid hexyl ester, methacrylic acid methyl ester, N-(methyl)acrylamide, acrylic acid-2-ethylhexyl ester, methacrylic acid-2-ethylhexyl ester, N-(2-ethylhexyl)acrylamide, acrylic acid octyl ester, methacrylic acid octyl ester, N-(octyl)acrylamide, acrylic acid lauryl ester, methacrylic acid lauryl ester, N-(lauryl)acrylamide, acrylic acid stearyl ester, methacrylic acid stearyl ester, N-(stearyl)acrylamide, acrylic acid behenyl ester, methacrylic acid behenyl ester and N-(behenyl)acrylamide, or mixtures thereof.

The proportion by weight of the sulfonic acid group-containing copolymers with respect to the total weight of cleaning agents is preferably from 0.1 to 15 wt. %, more preferably from 1.0 to 12 wt. % and in particular from 2.0 to 10 wt. %.

The cleaning agents can contain an organic solvent as a further component. Adding organic solvents has an advantageous effect on the enzyme stability and cleaning performance of these agents. Preferred organic solvents are derived from the group of monohydric or polyhydric alcohols, alkanolamines or glycol ethers. The solvents are preferably selected from ethanol, n-propanol or i-propanol, butanol, glycol, propanediol or butanediol, glycerol, diglycol, propyl diglycol or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether or propylene glycol propyl ether, dipropylene glycol methyl ether or dipropylene glycol ethyl ether, methoxytriglycol, ethoxytriglycol or butoxytriglycol, 1-butoxyethoxy-2-propanol, 3-methyl-3-methoxybutanol, propylene-glycol-t-butylether, and mixtures of these solvents. The proportion by weight of these organic solvents with respect to the total weight of the cleaning agents is preferably from 0.1 to 10 wt. %, more preferably from 0.2 to 8.0 wt. % and in particular from 0.5 to 5.0 wt. %. A particularly preferred organic solvent which is particularly effective in stabilizing the cleaning agents is glycerol, as well as 1,2-propylene glycol. Liquid cleaning agents which contain at least one polyol, preferably from the group of glycerol and 1,2-propylene glycol, wherein the proportion by weight of the polyol with respect to the total weight of the cleaning agent preferably is from 0.1 to 10 wt. %, more preferably from 0.2 to 8.0 wt. %, and in particular from 0.5 to 5.0 wt. %, are preferred. Other preferred organic solvents are the organic amines and alkanolamines. The cleaning agents preferably contain these amines in amounts of from 0.1 to 10 wt. %, more preferably from 0.2 to 8.0 wt. % and in particular from 0.5 to 5.0 wt. %, in each case based on the total weight thereof. A particularly preferred alkanolamine is ethanolamine.

Another preferred component of the cleaning agents is a sugar alcohol (alditol). The group of alditols includes non-cyclic polyols of the formula $HOCH_2[CH(OH)]_nCH_2OH$. The alditols include, e.g., mannitol, isomalt, lactitol, sorbitol and xylitol, threitol, erythritol and arabitol. Sorbitol has been found to be particularly advantageous with regard to enzyme stability. The proportion by weight of the sugar alcohol with respect to the total weight of the cleaning agent is preferably from 1.0 to 10 wt. %, more preferably from 2.0 to 8.0 wt. % and in particular from 3.0 to 6.0 wt. %.

An agent advantageously contains the protease in an amount of from 2 μg to 20 mg, preferably from 5 μg to 17.5 mg, more preferably from 20 μg to 15 mg and most particularly preferably from 50 μg to 10 mg per g of the agent. Further, the protease contained in the agent, and/or other ingredients of the agent, may be coated with a substance which is impermeable to the enzyme at room temperature or in the absence of water, and which becomes permeable to the enzyme under conditions of use of the agent. Such an embodiment is thus characterized in that the protease is coated with a substance which is impermeable to the protease at room temperature or in the absence of water. Furthermore, the cleaning agent itself can be packed in a container, preferably an air-permeable container, from which it is released shortly before use or during the washing process.

These embodiments include all solid, powdered, granular, tablet-form, liquid, gel or pasty administration forms of agents, which may optionally also consist of a plurality of phases and can be present in compressed or uncompressed form. The agent may be present as a flowable powder, in particular having a bulk density of from 300 g/L to 1200 g/L, in particular from 500 g/L to 900 g/L or from 600 g/L to 850 g/L. The solid dosage forms of the agent also include extrudates, granules, tablets or pouches containing solid agents, which can be present both in large containers and in portions. Alternatively, the agent may also be in liquid, gel or pasty form, for example in the form of a non-aqueous liquid washing agent or a non-aqueous paste or in the form of an aqueous liquid washing agent or a water-containing paste. The agent may also be present as a single-component system. Such agents consist of one phase. Alternatively, an agent may also consist of a plurality of phases (multi-component system). Such an agent is accordingly divided into several components, for example two liquid, two solid or one liquid and one solid phase. The water- and/or organic-solvent-based liquid product formats may be present in thickened form, namely in the form of gels.

A substance (e.g. a composition) or an agent is solid if it is in the solid physical state at 25° C. and 1,013 mbar.

A substance (e.g. a composition) or an agent is liquid if it is in the fluid physical state at 25° C. and 1,013 mbar. Liquid also includes gel form.

If the cleaning agents are present in liquid form, they preferably contain 40 wt. %, preferably between 50 and 90 wt. % and in particular between 60 and 80 wt. %, of water, based on the total weight thereof.

The cleaning agents described herein, in particular dishwashing agents, even more preferably automatic dishwashing agents, are preferably pre-packaged into dosing units. These dosing units preferably comprise the amount of active cleaning substances necessary for a cleaning cycle. Preferred dosing units have a weight between 12 and 30 g, preferably between 14 and 26 g and in particular between 15 and 22 g. The volume of the aforementioned dosing units and the spatial shape thereof are particularly preferably selected so that the pre-packaged units can be dosed via the dosing chamber of a dishwasher. The volume of the dosing unit is therefore preferably between 10 and 35 mL, preferably between 12 and 30 mL.

The automatic dishwashing agents, in particular the pre-fabricated dosing units, particularly preferably have a water-soluble wrapping. The water-soluble wrapping is preferably made from a water-soluble film material, which is selected from the group consisting of polymers or polymer mixtures. The wrapping may be made up of one or of two or more layers of the water-soluble film material. The water-soluble film material of the first layer and of the additional layers, if present, may be the same or different. Particularly preferred are films which, e.g., can be glued and/or sealed to form packaging such as tubes or sachets after they have been filled with an agent.

The water-soluble packaging may have one or more chambers. The agent may be contained in one or more chambers, if present, of the water-soluble wrapping. The amount of agent preferably corresponds to the full or half dose required for a dishwashing cycle.

It is preferable for the water-soluble wrapping to contain polyvinyl alcohol or a polyvinyl alcohol copolymer. Water-soluble wrappings containing polyvinyl alcohol or a polyvinyl alcohol copolymer exhibit good stability with a sufficiently high level of water solubility, in particular cold-water solubility. Suitable water-soluble films for producing the water-soluble wrapping are preferably based on a polyvinyl alcohol or a polyvinyl alcohol copolymer of which the molecular weight is in the range of from 5,000 to 1,000,000 g/mol, preferably from 20,000 to 500,000 g/mol, particularly preferably from 30,000 to 100,000 g/mol, and in particular from 40,000 to 80,000 g/mol. Suitable water-soluble films for use in the water-soluble wrappings of the water-soluble packaging are films which are sold by MonoSol LLC, e.g. under the names M8630, C8400 or M8900. Other suitable films include films under the names Solublon® PT, Solublon® GA, Solublon® KC or Solublon® KL from Aicello Chemical Europe GmbH, or the VF-HP films from Kuraray.

Such water-soluble wrappings are also already described in patent applications WO2004031338A and WO2003099985A, the disclosure of which is hereby incorporated by reference in its entirety.

The enzymes are generally not provided in the form of pure protein, but rather in the form of stabilized, storable and transportable preparations. These pre-packaged preparations include, e.g., the solid preparations obtained through granulation, extrusion, or lyophilization or, in particular in the case of liquid or gel agents, solutions of the enzymes, which are advantageously maximally concentrated, have a low water content, and/or are supplemented with stabilizers or other auxiliaries. Moreover, it is possible to formulate two or more enzymes together, such that a single granule exhibits a plurality of enzyme activities.

Cleaning agents may exclusively contain a *Bacillus gibsonii* protease, as defined herein. Alternatively, they may also contain other enzymes in a concentration that is expedient for the effectiveness of the agent. A further embodiment is therefore represented by agents which further comprise one or more further enzymes. Further enzymes which can preferably be used are all enzymes which can exhibit catalytic activity in the agent, in particular a lipase, amylase, cellulase, hemicellulase, mannanase, tannase, xylanase, xanthanase, xytoglucanase, β-glucosidase, pectinase, carrageenase, perhydrolase, oxidase, oxidoreductase or another protease, which is different from the proteases, as well as mixtures thereof. Enzymes are contained in the agent advantageously in an amount of from $1\times10^{-8}$ to 5 wt. % in each case, based on the active protein. Increasingly preferably, each further enzyme is contained in agents in an amount of from $1\times10^{-7}$ to 3 wt. %, from 0.00001 to 1 wt. %, from 0.00005 to 0.5 wt. %, from 0.0001 to 0.1 wt. % and particularly preferably from 0.0001 to 0.05 wt. %, based on active protein. Particularly preferably, the enzymes exhibit synergistic cleaning performance on specific stains or spots, i.e. the enzymes contained in the agent composition support one another in their cleaning performance. Very particularly preferably, there is such synergism between the protease contained and a further enzyme of an agent, including in particular between said protease and an amylase and/or a lipase. Synergistic effects may arise not only between different enzymes, but also between one or more enzymes and other ingredients of the agent.

Examples of proteases are the subtilisins BPN' from *Bacillus amyloliquefaciens* and Carlsberg from *Bacillus licheniformis*, protease PB92, subtilisins 147 and 309, the protease from *Bacillus lentus*, subtilisin DY, and the enzymes thermitase, proteinase K and proteases TW3 and TW7, which belong to the subtilases but no longer to the subtilisins in the narrower sense. Subtilisin Carlsberg is available in a further developed form under the trade name Alcalase® from the Novozymes company. The subtilisins 147 and 309 are sold by the Novozymes company under the trade names Esperase® and Savinase®, respectively. The protease variants marketed under the name BLAP® are derived from the protease from *Bacillus lentus* DSM 5483. Further usable proteases are, for example, enzymes available under the trade names Durazym®, Relase®, Everlase®, Nafizym®, Natalase®, Kannase® and Ovozyme® from the company Novozymes, which are sold under the trade names, Purafect®, Purafect® OxP, Purafect® Prime, Excellase® and Properase® by the company Danisco/Genencor, which is sold under the trade name Protosol® by the company Advanced Biochemicals Ltd., which is sold under the trade name Wuxi® by the company Wuxi Snyder Bioproducts Ltd., which is sold under the trade name Proleather® and Protease P® by Amano Pharmaceuticals Ltd., and under the name Proteinase K-16 by Kao Corp. The proteases from *Bacillus gibsonii* and *Bacillus pumilus*, disclosed in international patent applications WO2008086916 and WO2007131656 are particularly preferably used. Further advantageously usable proteases are disclosed in patent applications WO9102792, WO2008007319, WO9318140, WO0144452, GB1243784, WO9634946, WO2002029024 and WO2003057246. Further proteases that can be used are those which are naturally present in the microorganisms

*Stenotrophomonas maltophilia*, in particular *Stenotrophomonas maltophilia* K279a, *Bacillus intermedius* and *Bacillus sphaericus*.

Examples of amylases are α-amylases from *Bacillus licheniformis*, from *Bacillus amyloliquefaciens* or from *Bacillus stearothermophilus*, as well as in particular the developments thereof that have been improved for use in cleaning agents. The enzyme from *Bacillus licheniformis* is available from Novozymes under the name Termamyl® and from Danisco/Genencor under the name Purastar® ST. Development products of this α-amylase are available from Novozymes under the trade names Duramyl® and Termamyl® ultra, from Danisco/Genencor under the name Purastar® OxAm, and from Daiwa Seiko Inc., Tokyo, Japan, as Keistase®. The α-amylase from *Bacillus amyloliquefaciens* is marketed by Novozymes under the name BAN®, and derived variants from the α-amylase from *Bacillus stearothermophilus* are marketed under the names BSG® and Novamyl®, also by Novozymes. Furthermore, for this purpose the α-amylases from *Bacillus* sp. A 7-7 (DSM 12368) and the cyclodextrin glucanotransferase (CGTase) from *Bacillus agaradherens* (DSM 9948) should be emphasized. Furthermore, the amylolytic enzymes can be used which are disclosed in international patent applications WO2003002711, WO2003054177 and WO2007079938, the disclosure of which is therefore expressly referred to or the disclosure of which is therefore expressly included in the present patent application. Fusion products of all mentioned molecules can also be used. Furthermore, the developments of the α-amylase from *Aspergillus niger* and *A. oryzae*, available under the trade name Fungamyl® from Novozymes, are suitable. Other commercial products that can advantageously be used are, for example, Amylase-LT®, and Stainzyme® or Stainzyme Ultra® or Stainzyme Plus®, as well as Amplify™ or Amplify Prime™, also from Novozymes. Variants of these enzymes that can be obtained by point mutations may also be used.

Examples of lipases or cutinases, which are used in particular because of their triglyceride-cleaving activities, but also to generate peracids from suitable precursors in situ, include, for example, the lipases originally obtained from *Humicola lanuginosa* (*Thermomyces lanuginosus*) or further developed therefrom, in particular those with one or more of the following amino acid exchanges starting from the lipase mentioned in positions D96L, T213R and/or N233R, particularly preferably T213R and N233R. Lipases are sold, for example, by the Novozymes company under the trade names Lipolase®, Lipolase® Ultra, LipoPrime®, Lipozyme® and Lipex®. Another lipase that can be used advantageously is available from Novozymes under the trade name Lipoclean®. Moreover, the cutinases which have been originally isolated from *Fusarium solani pisi* and *Humicola insolens* can also be used, for example. Lipases that can also be used are available from Amano under the names Lipase CE®, Lipase P®, Lipase B®, and Lipase CES®, Lipase AKG®, *Bacillus* sp. Lipase®, Lipase AP®, Lipase M-AP® and Lipase AML®. From the company Danisco/Genencor, for example, lipases or cutinases can be used whose starting enzymes were originally isolated from *Pseudomonas mendocina* and *Fusarium solanii*. The preparations M1 Lipase® and Lipomax® originally marketed by Gist-Brocades (now Danisco/Genencor), the enzymes marketed by Meito Sangyo KK, under the names Lipase MY-30®, Lipase OF® and Lipase PL®, and the product Lumafast® from Genencor should be mentioned as other important commercial products.

In order to increase the bleaching effect, oxidoreductases such as oxidases, oxygenases, catalases, peroxidases such as halo-, chloro-, bromo-, lignin, glucose, or manganese peroxidases, dioxygenases or laccases (phenoloxidases, polyphenoloxidases) can be used. Advantageously, organic, particularly preferably aromatic compounds that interact with the enzymes are additionally added in order to enhance the activity of the relevant oxidoreductases (enhancers) or, in the event of greatly differing redox potentials, to ensure the flow of electrons between the oxidizing enzymes and the stains (mediators).

A further object is a method for cleaning hard surfaces, in particular dishware, characterized in that in at least one method step, an agent is used.

A preferred cleaning method is an automatic dishwashing method. The cleaning agent can be dispensed into the cleaning liquor in such a method for example by means of the dispensing chamber in the door or by means of an additional dispensing container in the interior of the dishwasher. Alternatively, the cleaning agent can also be applied directly to the dirty dishes or to one of the interior walls of the dishwasher, for example the inside of the door. The method is carried out in the interior of a commercially available dishwasher. In the case of a dishwasher, the cleaning program can generally be selected and determined by the user before the dishwashing method is carried out. The dishwasher cleaning program used in the method comprises at least one prewash cycle and one cleaning cycle. Cleaning programs which comprise further cleaning or rinsing cycles, e.g. a rinse cycle, are preferred. The method is particularly preferably part of a cleaning program comprising a prewash cycle, a cleaning cycle and a rinse cycle. The method is preferably used in connection with cleaning programs in which the washing liquor is heated during the cleaning cycle. In a preferred embodiment of the method, the cleaning cycle during which the cleaning agent is dispensed into the interior of the dishwasher is characterized in that the temperature of the cleaning liquor during said cycle rises to values above 30° C., preferably above 40° C. and in particular above 50° C.

In various embodiments, the method described above is characterized in that the protease is used at a temperature of from 0 to 100° C., preferably 10 to 70° C., more preferably 30 to 50° C. and most preferably at 45° C.

All aspects, objects and embodiments described for the protease and agents containing it are also applicable to the subject matter, corresponding methods and uses. Therefore, reference is expressly made at this point to the disclosure at the appropriate point with the note that this disclosure also applies to the above-described use.

Examples

Determination of the Cleaning Performance of Dishwashing Agents

The cleaning performance of a commercial automatic dishwashing agent in the form of a dishwashing agent tablet, which contained 15 wt. % sodium percarbonate as hydrogen peroxide source (bleach), 0.03 wt. % Mn-Me-TACN (Mn-TACN) as a bleach catalyst and 2.2 wt. % TAED as a bleach activator was tested, to which protease granules 1 or 2 were added in each case. The proteases were each used with the same active protein.

The cleaning performance was determined in accordance with the IKW method in a Miele GSL dishwasher (program: 45° C., water hardness 21° dH). The dishwashing agent tablet was placed in the dosing device before the start of the cleaning program. Three determinations were carried out in each case, the results of which were averaged in each case. The cleaning performance is evaluated visually according to a scale from 1 to 10, with the value 10 being the best rating (no discernible residue). Values are considered significant if the improvement is at least 1.0. The results are shown in the tables below.

TABLE 1

|  |  | Burnt-in ground meat | Egg yolk | Tea (Assam) | Tea (BOP) |
|---|---|---|---|---|---|
| E1 | Dishwashing agent with protease granulate 1 (30 mg/job) | 6.5 | 5.2 | 6.8 | 7.5 |
| E2 | Dishwashing agent with protease granulate 2 (30 mg/job) | 5.2 | 4.1 | 6.0 | 5.9 |

TABLE 2

|  |  | Crème brulée | Egg yolk | Tea (Assam) | Tea (BOP) |
|---|---|---|---|---|---|
| E3 | Dishwashing agent with protease granulate 1 (120 mg/job) | 9.1 | 8.4 | 7.3 | 7.5 |
| E4 | Dishwashing agent with protease granulate 2 (120 mg/job) | 7.7 | 6.9 | 6.3 | 6.7 |

TABLE 3

|  |  | Crème brulée | Tea (Assam) |
|---|---|---|---|
| E5 | Dishwashing agent with protease granulate 1 (220 mg/job) | 9.7 | 7.6 |
| E6 | Dishwashing agent with protease granulate 2 (220 mg/job) | 8.6 | 6.3 |

Protease granules 1 contain a protease according to SEQ ID NO: 5 described in WO2017215925.

Protease granulate 2 contains a combination of protease 2a (protease according to SEQ ID NO: 6 from WO2016000973) and protease 2b (Ovozyme®, ex Novozymes) in a ratio of 1.5:1.

Surprisingly, it has been found that when protease granulate 1 is used, in addition to a significantly improved cleaning performance on protein-containing stains, a significantly improved cleaning performance on tea stains can also be observed.

The invention claimed is:

1. A dishwashing detergent comprising:

a hydrogen peroxide source;

a bleach catalyst selected from the group consisting of a complex of manganese with 1,4,7-trimethyl-1,4,7-triazacyclononane (Me-TACN) and a complex of manganese with 1,2,4,7-tetramethyl-1,4,7-triazacyclononane (Me/Me-TACN); and a protease comprising an amino acid sequence having at least 98.8% sequence identity with the amino acid sequence given in SEQ ID NO: 1 over its entire length, wherein the protease comprises the following amino acid substitution variant: (i) M211L and P212D, wherein the numbering is based on the numbering according to SEQ ID NO: 1.

2. The dishwashing detergent of claim 1, wherein the hydrogen peroxide source is selected from the group consisting of sodium percarbonate, sodium perborate tetrahydrate, sodium perborate monohydrate, and any combination thereof.

3. The dishwashing detergent of claim 1, wherein the protease is present in an amount ranging from $1 \times 10^{-8}$ to 10 wt. %, based on the active protein content of the protease.

4. The dishwashing detergent of claim 1, wherein the detergent is a machine dishwashing detergent.

5. The dishwashing detergent of claim 1, further comprising at least one ingredient selected from the group consisting of a builder, a tenside, an anionic polymer, an enzyme, and any combination thereof.

6. A method for removing a protein-containing stain on a hard surface, the method comprising:

contacting the hard surface with a cleaning composition comprising the dishwashing detergent of claim 1.

7. The dishwashing detergent of claim 1, wherein the bleach catalyst is present in an amount ranging from 0.0025 wt. % to 1 wt. %, based on the total weight of the dishwashing detergent.

8. The dishwashing detergent of claim 1, wherein the hydrogen peroxide source is present in an amount ranging from 2 wt. % to 30 wt. %, based on the total weight of the dishwashing detergent.

9. The dishwashing detergent of claim 8, wherein the hydrogen peroxide source is present in an amount ranging from 6 wt. % to 15 wt. %, based on the total weight of the dishwashing detergent.

10. The dishwashing detergent of claim 1, further comprising tetraacetylethyl ethylenediamine (TAED).

11. The dishwashing detergent of claim 5, wherein the enzyme comprises an ingredient selected from the group consisting of a protease, an amylase, a cellulase, a pectin-splitting enzyme, a hemicellulase, a mannanase, a tannase, a xylanase, a xanthanase, a β-glucosidase, a carrageenase, a perhydrolase, an oxidase, an oxidoreductase, a lipase, and any combination thereof.

12. The dishwashing detergent of claim 11, wherein the enzyme is an enzyme combination selected from the group consisting of a protease and an amylase, a protease and a lipase, a protease and a cellulose, a protease and a mannanase, an amylase and a lipase, an amylase and a cellulose, an amylase and a mannanase, a lipase and a cellulose, a lipase and a mannanase, a lipase and a cellulose, a protease, an amylase and a lipase, a protease, an amylase and a cellulose, a protease, an amylase and a mannanase, an amylase, a lipase and a cellulose, an amylase, a lipase and a mannanase, a lipase, a cellulase and a mannanase, a protease, an amylase, a lipase and a cellulose, and a protease, and an amylase, a cellulase and a mannanase.

13. The dishwashing detergent of claim 1, wherein the hydrogen peroxide source is sodium percarbonate.

14. A dishwashing detergent comprising:
sodium percarbonate;
a complex of manganese with 1,4,7-trimethyl-1,4,7-tri-azacyclononane (Me-TACN); and
a protease comprising an amino acid sequence having at least 98.8% sequence identity with the amino acid sequence given in SEQ ID NO: 1 over its entire length, wherein the protease comprises the following amino acid substitution variant: (i) M211L and P212D, wherein the numbering is based on the numbering according to SEQ ID NO: 1.

15. The dishwashing detergent of claim 14, further comprising tetraacetylethyl ethylenediamine (TAED).

* * * * *